United States Patent [19]

Ågerup

[11] Patent Number: 5,633,001
[45] Date of Patent: May 27, 1997

[54] COMPOSITION AND A METHOD FOR TISSUE AUGMENTATION

[75] Inventor: Bengt Ågerup, Uppsala, Sweden

[73] Assignee: Medinvent, Uppsala, Sweden

[21] Appl. No.: 525,558

[22] PCT Filed: Jan. 27, 1994

[86] PCT No.: PCT/SE94/00060

§ 371 Date: Sep. 19, 1995

§ 102(e) Date: Sep. 19, 1995

[87] PCT Pub. No.: WO94/21299

PCT Pub. Date: Sep. 29, 1994

(Under 37 CFR 1.47)

[51] Int. Cl.$^6$ ............................ A61F 2/02; A61K 47/30
[52] U.S. Cl. ................ 424/423; 514/772.3; 514/777
[58] Field of Search ................ 424/423; 514/772.3, 514/777

[56] References Cited

U.S. PATENT DOCUMENTS

| | | | |
|---|---|---|---|
| 4,197,846 | 4/1980 | Bucalo | 604/51 |
| 4,716,154 | 12/1987 | Mälson et al. | 514/54 |
| 4,767,463 | 8/1988 | Brode et al. | 106/162 |
| 4,777,200 | 10/1988 | Dymond et al. | 524/458 |
| 4,803,075 | 2/1989 | Wallace | 424/423 |
| 5,007,940 | 4/1991 | Berg | 623/66 |
| 5,017,229 | 5/1991 | Burns et al. | 106/162 |
| 5,128,326 | 7/1992 | Balazs et al. | 514/54 |
| 5,143,724 | 9/1992 | Leshchiner et al. | 424/78.08 |
| 5,399,351 | 3/1995 | Leshchiner et al. | 424/422 |

FOREIGN PATENT DOCUMENTS

| | | |
|---|---|---|
| 0 161 887 | 11/1985 | European Pat. Off. . |
| 0 265 116 | 4/1988 | European Pat. Off. . |
| 0 402 031 | 12/1990 | European Pat. Off. . |
| 0 466 300 | 1/1992 | European Pat. Off. . |
| 460 792 | 11/1989 | Sweden . |
| 2 205 848 | 12/1988 | United Kingdom . |
| WO 87/07898 | 12/1987 | WIPO . |
| WO 91/05544 | 5/1991 | WIPO . |
| WO 94/02184 | 2/1994 | WIPO . |
| WO 94/21299 | 9/1994 | WIPO . |

OTHER PUBLICATIONS

"Inflammation Responsive Degradation of Cross–Linked Hyaluronic Acid Gels", *Journal of Controlled Release*, Nobuhijo Yui et al., 22 (1992), pp. 105–116.

"Cross–Linked Gels of Hyaluronic Acid", Torvard C. Laurent et al., Acta Chem. Scand., No. 1, p. 274, (1964).

*Primary Examiner*—Carlos A. Azpuru
*Attorney, Agent, or Firm*—Burns, Doane, Swecker & Mathis, L.L.P.

[57] ABSTRACT

The present invention provides a biocompatible composition for tissue augmentation, comprising a pseudoplastic polymer carrier in an amount of 0.05–50% (w/w) of the total composition; and one or more tissue augmenting substances (s). Furthermore, the invention comprises a method for tissue augmentation, comprising: injecting the above composition into a desired site of the human or animal body for augmenting the tissue at and around said site.

21 Claims, No Drawings

COMPOSITION AND A METHOD FOR TISSUE AUGMENTATION

BACKGROUND OF THE INVENTION

The present invention relates to a composition and a method for tissue augmentation.

Tissue augmentation is desirable for both therapeutical and cosmetical purposes. A therapeutical application is, for example, augmentation of tissues that need to be enlarged for proper function. Examples of such are the vocal cords, the oesophagus, various sphinters that have become weakened or have too thin tissue mass. Another set of examples are enlargement of the muscles of, for instance, the urether and rectum. In the field of cosmetic surgery tissue augmentation is applied to wrinkles and scars as well as to enlarge lips or fill out age related diminished fat deposits around the eyes as well as other applications. In the cosmetical field, plastic surgeons fill out, for example, eye wrinkles, by injecting tissue augmenting materials.

Materials used for augmentation of tissues are, for instance, the patients own fat cell cartilage or other suitable materials. Commercially available biologically degradable materials include collagen suspensions and crosslinked hyaluronic acid. Non degradable materials include silicone oil, silicone microparticles, Teflon® paste and other inert materials.

U.S. Pat. No. 5,007,940 teaches the use of deformable, nonbiodegradable hydrogels with a lubricious surface. The patent concerns injecting of nonbiodegradable material which appears by the finding of such material in the brain tissues. Thus any material injected into tissues has a risk of being carried away by the venous blood to central parts of the body. For individuals with a life expectancy of several years this is not likely to be accepted by regulatory authorities. Therefore, such materials are presently not widely used due to migration to critical tissues or long term negative reactions on the health like autoimmune diseases or cancer.

Homotransplantation of tissue is a cumbersome and painful procedure that has a too short action. The most frequently used material today is collagen suspension. However it is made from bovine collagen and can carry unwanted slow action viruses. Most negative is the fact that some patients develop a sensitivity towards the material or get stimulated enzymatic activity in the skin due to repeated foreign body reactions. Despite these drawbacks the products are still very popular. An interesting new product under clinical evaluation is a crosslinked form of hyaluronic acid.

U.S. Pat. No. 5,143,724 teaches the use of viscoelastic gel slurries of high biocompatibility. The patent relates to materials based on hyaluronic acid or s.c. hylans with very low cell interaction which is very useful in some applications but which has a limited value in tissue augmentation uses. The reason is because these materials will spread out in the tissue and loose it's augmenting property.

From the above it appears that the existing materials are clearly not ideal end the search for new improved materials for tissue augmentation continues with the aim to identify materials that are biocompatible, injectable through thin needles, non health threatening and has a residence time in tissues—short enough to disappear when their function is no longer desirable but long enough to be worth the effort to make the implantation.

The present invention addresses this aspect as well as that of versatility in designing an ideal composition for a specific tissue that needs to be augmented. In addition, these same compositions have proven to be very useful vehicles for the delivery of drugs.

SUMMARY OF THE INVENTION

The present invention provides for a composition for tissue augmentation that allows for a rich variety of polymers to be injected through thin or long needles into desired position in the human or animal body. The implanted polymers can be composed to create different configurations in the tissue from very round ball-type forms to flat sheet formed implants. All this for the purpose of providing an optimal cosmetic result or therapeutic effect.

Although these conditions requiring tissue augmentation have been recognized for years and therapeutical and cosmetical solutions exist for the treatment thereof, the present invention provides novel compositions in the search for effective such treatment.

It is an object of the present invention, therefore, to provide novel compositions for tissue augmentation comprising a carrier gel having pseudoplastic (shear thinning) properties and one or more biocompatible, tissue augmenting substance(s).

It is yet another object of this invention to provide a composition for tissue augmentation in which the augmentation is partly by its ability to act as an in vivo cell specific stimulator of cell proliferation to develop specific types of tissues such as connective tissue, smooth muscles and more.

Another object of the invention is to provide a composition with the ability to evoke an immune response or even to develop specific glandular functions.

Yet another object of the present invention is to provide the above composition with one or more therapeutically active ingredient(s).

It is a further object of the present invention to provide novel methods for tissue augmentation of desired tissues of the human or animal body, giving a long lasting effect and no serious side effects.

These and further objects will become apparent by the below provided detailed description of the invention.

DETAILED DESCRIPTION OF THE INVENTION

The biocompatible carrier gel of the composition according to the invention comprises a polymer dissolved in a suitable solution, such as physiological saline, as a matrix. The polymer is selected from the group consisting of glucose amine glucans, such as hyaluronic acid, hydroxy ethyl cellulose, carboxy methyl cellulose, xantahn gum, and alginates. Preferably, the matrix comprises 0.05–50% (w/w) of the composition. This carrier gel according to the invention has pseudoplastic properties, ie it has shear thinning properties.

The tissue augmenting substance of the composition according to the invention comprises water insoluble, biodegradable and biocompatible polymers. Examples of suitable polymers are collagen, starch, dextranomer, polylactide and copolymers thereof, poly-β-hydroxybutyrate and copolymers thereof.

The pseudoplastic properties of the carrier gel enables effective dispersion of the tissue augmenting substance therein. The dispersion can be formed at the time of injection or as a prefabricated formulation. In some cases it is also desirable for the composition to comprise one or more therapeutically active ingredient(s).

The active ingredient is selected from growth modulating factors, hormones, vaccines, cytokines, bacteriostatic or bacteriocidal agents or antiviral agents and other pharmacologically active compounds.

Furthermore the invention provides a method for tissue augmentation, comprising: injecting a composition described above into a desired site of the human or animal body for augmenting the tissue around said site.

This method also involves injecting the tissue augmentation material under fiberoptic guidance through long cannulas or catheters. In both cases, the pseudoplastic carrier is the most effective means to carry particulate polymers to a desired site, forming a right configuration and avoiding sedimentation or piling up the polymer in the injection system. The physical configuration is also an essential component in obtaining an optimal release rate from a sustained release preparation of active ingredient. In the case further augmentation is needed, the method is repeated after a certain time period from the first injection.

In a recent set of clinical investigations we also noticed an additional benefit of some of the augmenting substances. When analysing the tissue samples obtained at a second intervention of the patients, we noticed that depending on which type of augmenting microparticles used specific cells were recruited to the surface of the particles. Thus we also see a benefit of being able to augment the tissue by stimulating specific cells to proliferate and grow on the surface of the particles or to be recruited to a specific site of the body and there produce special materials such as collagen, growth stimulators, interferon and more. These techniques are partly known from the art of cell biology. This will be made much clearer in connection with the experimental part below.

The augmenting substance referred to in the present description is sometimes called microcarier having the equivalent meaning.

The invention will be disclosed in greater detail below in association with some non limiting Examples.

EXAMPLES

Example 1

1 gram of a fractionated size-defined medical grade dextranomer as augmenting substance was mixed with 100 mg of a high molecular weight hyaluronan fiber. To the mixture was added 25 ml of saline. The composition was dispersed into suitable syringes and heat sterilized for 20 minutes. The resulting slurry was then injected through a 30 gauge needle subcutaneously and the shape of the bolus was found to be very formable. After three to four weeks, histologic examination revealed a good integration of the dextran spheres with only a mild foreign body reaction. The pseudoplastic carrier had been reabsorbed.

Example 2

100 mg of an alginate (Pronova UP MVG) was dissolved in 5 grams of physiological saline solution to yield a highly viscous and pseudoplastic solution. To this solution was added 1 gram of a powder of poly-β-hydroxybutyrate as augmenting substance. The resulting slurry was injected under the skin of a nude mouse. A ball-shaped bolus was formed. The bolus was made harder by immediate follow-up of an injection of a 0.15M calcium chloride solution.

Example 3

1 gram of collagen for use as augmenting substance was subjected to pepsin digestion and glutaraldehyde crosslinking and grinded to small 100 μm fragments. The slurry was made up to 25 ml of total volume by adding physiological saline. To the slurry was added 100 mg of high molecular weight hyaluronan fiber and 2.5 mg of lidocaine and adrenaline. The pseudoplastic fluid was transferred to syringes and injected subcutaneously into 5 healthy students. The composition was easy to inject and formed a distinct bolus. There was a short flash of pain upon injection but no bleeding. The augmented tissue was present for about 6 months (range 3–10). No adverse reaction was noticed.

Example 4

1 gram of cross-linked starch in the form of fibers was grinded to 100 μm fibers. The resulting ageous slurry (25 ml) was heat sterilized and mixed with 100 mg of high molecular weight hyaluronan fibers. The reslutant pseudoplastic slurry was injected subcutaneously into nude mice. The augmentation lasted for more than 12 months as extrapolated from the 3 months evaluation. There was no sign of tissue reaction.

Example 5

1 gram of cross-linked starch in the form of microspheres (Spherex® Kabi-Pharmacia) was mixed with 20 ml of a 1% hyaluronan solution (Hylartil® Pherrovet) and injected in the urether of a woman suffering from a mild form of incontinence. After six weeks, the incontinence returned to its pretreatment condition.

Example 6

The same woman as in Example 5 was subjected to a new treatment with an improved composition. Now, 1 gram of dextranomer (G 25 Ultrafine Sephadex® Kabi Pharmacia) was thoroughly washed until tested non-irritating followed by sterilization by heat. The microbeads were mixed with 20 ml of a 1% solution of hyaluronan. Approximately 6 ml was injected in the urether under fiber optic guidance. After three weeks and additional 4 ml were injected as the previous treatment was considered inadequate.

At one year follow up, the woman was still continent and had no problem with the treatment.

Example 7

100 mg of a medical grade alginate (Pronova MGM) was dissolved in 20 ml of a balanced salt solution. To the viscous fluid was added 1 mg tranexam acid (a haemostatic agent) and 1 gram of dextranomer (as in Example 6). The resulting slurry was injected in the lip of a patient undergoing treatment for cosmetic surgery. The 3 months result showed that the augmentation was still present and the muscles of The lips were soft and homogeneous.

Example 8

In connection with the reconstruction of the root of a tooth it was noted that the epithelial lining of the attachment site was digested by bacterial enzymes. Surgery was performed and the area was cleaned and small holes were drilled in the bone adjacent to the reconstruction. A membrane was put to protect from overgrowth by the gingiva and under the membrane an augmenting microcarrier was injected with the following composition:

DEAE-Sephadex 50 mg/ml, size<120 μm in isotonic buffer pH 7,4.

The blood was allowed to drain into the microcarrier suspension prior to closing of the wound.

At three months follow up a hard connective tissue was formed that later development into complete bone.

The fibroblasts known to attach to the microcarrier had been transformed to osteoblasts.

Example 9

Children suffering from vesicoureteral reflux can be cured by augmenting the tissue with the following composition:

Sephadex 50 mg/ml
Hyaluronic acid 12 mg/ml
pH 7,4

This composition was injected in the bladder wall at the orifice of the urether of children suffering from vesicouretheral reflux. A market stimulation of fibroblast proliferation and synthesis of collagen was noted already at two weeks after implantation. The result was that the reflux was completely stopped in 76% of the patients and improved in 10%.

Example 10

In an attempt to fill out wrinkles in the face of a woman the following composition was developed.

Dextranomer (Sephadex®) was suspended in a 0,5% solution of kitosan N-deacetylated at 85%. It was sucked dry by air and mixed at equal volumes with a 0,5% solution of a high molecular weight formulation of hyaluronic acid. The so formed suspension was injected intradermally just at the wrinkle bottom with a thin needle. The augmented portion of the skin showed at three months follow up a soft smoothening of the wrinkle with essentially no tissue reaction. At biopsy the tissue specimen showed no sign of a foreign body reaction but a small ingrowth of collagen type II.

Example 11

A face with multiple scars from an earlier acne period was treated by subcutaneous injections of a formulation with the following composition. Sephadex® 50 mg/ml coated with kitosan 50% N-deacetylated. The coated Sephadex microspheres were suspended in a 0,5% heparin solution for 30 minutes at pH 8. A test with toulidine blue showed a marked colour of the dried microspheres indicating a high degree of surface coating of heparin. Inoculation of the mixture with EGF showed a high degree of binding to the microspheres. The resultant combination was injected as initially described.

The result showed a marked reduction of the acne scars at three months follow-up.

Example 12

An a-v port designed to allow quick and easy connection to the blood stream was surgically put in place. Previous trials had shown that the port was associated with coagulation complications and also by overgrowth of endothelial cells. To condition the port the following modifications was made. At the contact sites of the vessel a multilayer of kitosan and heparin was applied. At the site of the movable parts a multilayer of kitosan and hyaluronic acid was applied. The results were that the overgrowth and coagulation problems were abolished for at least three months.

From the above it appears that the compositions and methods according to the present invention are suitable for therapeutical as well as cosmetical surgery for tissue augmenting purposes.

I claim:

1. A biocompatible composition which provides for tissue augmentation, which comprises
   (i) a pseudoplastic polymer carrier 0.05–50% (w/w) of the total composition; and
   (ii) a water insoluble, biocompatible and biodegradable tissue augmenting substance comprising a dextranomer.

2. A composition according to claim 1, wherein said pseudoplastic polymer carrier is selected from the group consisting of glucose amine glucans, hydroxy ethyl cellulose, carboxy methyl cellulose, xanthan gum, and alginates.

3. A composition according to claim 1, wherein said dextranomer is present in the form of microbeads.

4. A composition according to claim 1, wherein such tissue augmenting dextranomer is surface modified under conditions which result in a substance which stimulates or inhibits the growth of specific cell types.

5. A composition according to claim 1, which also comprises one or more therapeutically active ingredient(s).

6. A composition according to claim 5, wherein said active ingredient(s) is (are) in sustained release form.

7. A method for tissue augmentation, comprising:
   injecting a composition of a pseudoplastic carrier comprising a tissue augmenting material comprising dextranomer and optionally an active ingredient into a desired site on the human or animal body for augmenting the tissue at and around said site.

8. A method according to claim 7, comprising injecting said composition through a cannula or catheter under fiberoptic guidance.

9. A method according to claim 7, comprising repeating said injection after a certain time period in order to provide for further tissue augmentation.

10. A method for tissue augmentation comprising injecting a composition of a pseudoplastic carrier comprising a tissue augmenting material comprising dextranomer into a desired site on the human or animal body for augmenting the tissue at and around said site wherein the composition is as defined in claim 2.

11. A composition according to claim 2, wherein said dextranomer is present in the form of microbeads.

12. A composition according to claim 2, wherein said tissue augmenting dextranomer is surface modified under conditions which result in a substance which stimulates or inhibits the growth of specific cell types.

13. A composition according to claim 3, wherein said tissue augmenting dextranomer is surface modified under conditions which result in a substance which stimulates or inhibits the growth of specific cell types.

14. A composition according to claim 11, wherein said tissue augmenting dextranomer is surface modified under conditions which result in a substance which stimulates or inhibits the growth of specific cell types.

15. A composition according to claim 2, which also comprises one or more therapeutically active ingredients.

16. A composition according to claim 3, which also comprises one or more therapeutically active ingredients.

17. A composition according to claim 4, which also comprises one or more therapeutically active ingredients.

18. A composition according to claim 11, which also comprises one or more therapeutically active ingredients.

19. A composition according to claim 14, which also comprises one or more therapeutically active ingredients.

20. A method according to claim 8, comprising repeating said injection after a certain time period in order to provide for further tissue augmentation.

21. The composition of claim 2, wherein the glucose amine glucans comprise hyaluronic acid.

* * * * *

UNITED STATES PATENT AND TRADEMARK OFFICE
CERTIFICATE OF CORRECTION

PATENT NO. : 5,633,001
DATED : MAY 27, 1997
INVENTOR(S) : BENGT ÅGERUP

It is certified that error appears in the above-indentified patent and that said Letters Patent is hereby corrected as shown below:

On the face of the patent, before [51], please delete "(Under 37 CFR 1.47)".

Signed and Sealed this

Twentieth Day of January, 1998

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,633,001
DATED : MAY 27, 1997
INVENTOR(S) : BENGT ÅGERUP

It is certified that error appears in the above-identified patent and that said Letters Patent is hereby corrected as shown below:

Column 1, prior to the section entitled "BACKGROUND OF THE INVENTION", please insert:

-- Cross Reference to Related Application

This application claims the benefit pursuant 35 U.S.C. 120 for U.S. application Ser. No. 08/034,442, filed March 19, 1993 (now abandoned).-- , not including the PCT data for filing under 371.

Signed and Sealed this

Twenty-fourth Day of February, 1998

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,633,001
APPLICATION NO. : 08/525558
DATED : May 27, 1997
INVENTOR(S) : Bengt Ågerup It is certified that error appears in the above-identified patent and that said Letters Patent is hereby corrected as shown below:

Column 1, prior to the section entitled "BACKGROUND OF THE INVENTION", please insert:

-- Cross Reference to Related Application

This application claims the benefit pursuant 35 U.S.C. 120 for U.S. application Ser. No. 08/034,422, filed March 19, 1993 (now abandoned), --, not including the PCT data for filing under 371.

This certificate supersedes the Certificate of Correction issued February 24, 1998.

Signed and Sealed this

Seventeenth Day of February, 2009

JOHN DOLL
*Acting Director of the United States Patent and Trademark Office*